(12) United States Patent
DiSanzo et al.

(10) Patent No.: US 9,063,115 B2
(45) Date of Patent: Jun. 23, 2015

(54) METHOD FOR MONITORING REFINERY REFORMING UNITS UTILIZING DETAILED HYDROCARBON COMPOSITION ANALYSIS

(71) Applicants: Frank DiSanzo, Cherry Hill, NJ (US); Eric Shu Shi, Singapore (SG); Geok Ling Tan, Singapore (SG); Yoichi Y Sano, Wakayama (JP)

(72) Inventors: Frank DiSanzo, Cherry Hill, NJ (US); Eric Shu Shi, Singapore (SG); Geok Ling Tan, Singapore (SG); Yoichi Y Sano, Wakayama (JP)

(73) Assignee: ExxonMobil Research and Engineering Company, Annandale, NJ (US)

( * ) Notice: Subject to any disclaimer, the term of this patent is extended or adjusted under 35 U.S.C. 154(b) by 133 days.

(21) Appl. No.: 13/896,485

(22) Filed: May 17, 2013

(65) Prior Publication Data
US 2013/0323853 A1     Dec. 5, 2013

Related U.S. Application Data

(60) Provisional application No. 61/653,023, filed on May 30, 2013.

(51) Int. Cl.
*G01N 33/28*     (2006.01)
*C10G 35/24*     (2006.01)

(52) U.S. Cl.
CPC ............. *G01N 33/28* (2013.01); *Y10T 436/212* (2015.01); *C10G 35/24* (2013.01)

(58) Field of Classification Search
CPC ...... C10G 35/24; G01N 33/28; Y10T 436/24; Y10T 436/212
USPC .............. 436/60, 139, 140, 141, 161; 422/89; 208/88, 89
See application file for complete search history.

(56) References Cited

U.S. PATENT DOCUMENTS 7,805,979 B2 *  10/2010  Reddy et al. ................. 73/23.38
2009/0105966 A1   4/2009  Brown et al.

OTHER PUBLICATIONS

Vendeuvre et al. Journal of Chromatography A, vol. 1056, 2004, pp. 155-162.*
Briker et al., "Diesel Fuel Analysis by GC-Fims: Aromatics, n-Paraffins, and Isoparaffins", Energy & Fuels, vol. 15, pp. 23-37 (2001).
DeHouche et al., "New Correlations for Octane Number Prediction of Gasoline Using GPC Analysis", Journal de la Societe Algerienne de Chimie, vol. 18, No. 2, pp. 115-125 (2008).
Garcia et al., "In-Depth Modeling of Gas Oil Hydrotreating: From Feedstock Reconstruction to Reactor Stability Analysis", Catalysts Today, vol. 150, pp. 279-299 (2010).
Liu et al., "Determination of Vapour Pressure of Gasoline by Double ANN Algorithm Combined With Multidimensional Gas Chromatography", Centre of Technique, Dalian, China, pp. 1-3.
PCT Search Report issued Sep. 18, 2013 in PCT/US2013/042570 (4 pp.).
PCT Written Opinion issued Sep. 18, 2013 in PCT/US2013/042570 (5 pp.).

* cited by examiner

*Primary Examiner* — Maureen Wallenhorst
(74) *Attorney, Agent, or Firm* — Glenn T. Barrett; Andrew T. Ward

(57) ABSTRACT

A method of monitoring a reformer unit is disclosed. The method includes analyzing at least one of the feedstock and the product stream. The analyzing includes performing a detailed hydrocarbon analysis of at least one of the feedstock and the product stream. The method further includes obtaining a one-dimensional output from the detailed hydrocarbon analysis and adjusting the one-dimensional output to produce a multi-dimensional equivalent output. Adjusting the one-dimensional output includes applying an appropriate correlation matrix to the one-dimensional output to produce the multi-dimensional equivalent output. The appropriate correlation matrix is selected based upon the characteristics of the feedstock and the particular refinery unit.

23 Claims, No Drawings

METHOD FOR MONITORING REFINERY REFORMING UNITS UTILIZING DETAILED HYDROCARBON COMPOSITION ANALYSIS

FIELD

The present invention relates to the monitoring of refinery reforming units utilizing detailed hydrocarbon composition analysis. In particular, the present invention relates to the modification of the hydrocarbon analysis to improve the monitoring and optimization of the refinery reforming units.

BACKGROUND

In today's refining environment, the economics of operating a refinery unit (e.g. a reformer) depends on the proper selection of feedstocks and the real time optimization of refinery unit output profile in response to changing market conditions. Both the selection of feedstock and the optimization of output profile depend on timely analysis of the feedstock composition and product output. Such monitoring may involve inputting composition data into mathematical models to monitor the performance of the process units.

Refineries periodically monitor reformer units by performing detailed analyses of feeds and products. The most accurate manner to perform such analysis is to use a complex gas chromatographic analyzer using multi-columns (i.e. multi-dimensional) approach. Such analysis has also been called PIONA analysis. The analyzers performing PIONA analysis can be more costly, require higher maintenance than simpler one-dimensional gas chromatographic analysis based on a single boiling point type of capillary column and detection by flame ionization detection. The one dimensional analysis is called detailed hydrocarbon analysis (DHA). Therefore, there are advantages using the simplified DHA in a laboratory (less cost, easier to maintain and operate, provide detailed data for lower carbon number hydrocarbon species, etc.).

Comparison of the test reports, generated by PIONA and DHA separately but on the same sample, reveal variances in the amount of specific compounds contained in the feedstock. For example, there may be up to an approximately >5% difference in naphthene content, a >3% difference in paraffin content and a >2% difference in aromatics content, between the PIONA and DHA analyses. These variances translate into potential multi-million dollar losses of margin improvement, per year, per reformer when DHA analysis is used to monitor reformer unit operation compared to the use of PIONA analysis. There is a need to improve the accuracy of reformer units using less costly DHA analysis.

SUMMARY

The purpose and advantages of the present application will be set forth in and apparent from the description that follows, as well as will be learned by practice of the disclosed subject matter. Additional advantages of the disclosed subject matter will be realized and attained by the method and system particularly pointed out in the written description and claims hereof.

According to one aspect of the present application, the presently disclosed subject matter is directed to the development of correlation matrices between less accurate detailed hydrocarbon analysis (DHA) test results obtained by single capillary gas chromatographic analysis and their corresponding more complex but more accurate test results obtained by a multidimentional gas chromatographic analyses (PIONA). The deployment of the established correlation matrices to the day-to-day DHA test data analysis of changing feed and reforming products will then allow the less precise DHA testing results, widely available in most refineries, to be re-expressed in the form of more precise PIONA counterparts compositional analysis, that is, the correlation matrices function as multi-dimensional correction factors, to "convert" the DHA data to the PIONA data.

The presently disclosed subject matter is directed to a method of monitoring a refinery unit. The refinery contains various refinery units for processing hydrocarbons. One such refinery unit is a reformer unit which is used to transform lower octane molecules into higher octane molecules. The refinery unit has a feedstock supplied thereto and at least one product stream withdrawn therefrom. The feedstock may include various streams that are simultaneously fed to the refinery unit. The streams include in-process hydrocarbon streams that are produced within the refinery and purchased streams (e.g., purchased naphtha streams). The in-process streams and the purchased streams are collectively referred to as feedstock(s). In accordance with aspects of the present invention, the refinery unit is preferably a reformer unit. In accordance with the aspects of the present invention, the feedstock is preferably a naphtha feedstock. The method includes analyzing at least one of the feedstock and the product stream. The analyzing includes performing a detailed hydrocarbon analysis of at least one of the feedstock and the product stream. Preferably, the feedstock is analyzed. The method further includes obtaining a one-dimensional output from the detailed hydrocarbon analysis and adjusting the one-dimensional output to produce a multi-dimensional equivalent output. Adjusting the one-dimensional output includes applying an appropriate correlation matrix to the one-dimensional output to produce the multi-dimensional equivalent output. The appropriate correlation matrix is selected based upon the characteristics of the feedstock and the particular refinery unit. The location of the reformer unit within the refinery including the piping details leading to the reformer unit also impact the selection of the appropriate correlation matrix.

The presently disclosed subject matter is further directed to a method of optimizing the operation of the refinery unit based upon the multi-dimensional equivalent output. The multi-dimensional equivalent output is input in a unit performance model to optimize the operation of the refinery unit. The optimization is based upon obtaining an output from the unit performance model and adjusting the operation of the refinery unit based upon the output from the unit performance model.

The presently disclosed subject matter is further directed to a method of adjusting the operation of the refinery unit based upon the multi-dimensional equivalent output to adjust product output from the refinery unit. The multi-dimensional equivalent output is input in a unit performance model to modify the operation of the refinery unit to modify the product stream from the refinery unit. The modification of the operation is based upon obtaining an output from the unit performance model and adjusting the operation of the refinery unit based upon the output from the unit performance model.

DETAILED DESCRIPTION

While the disclosed subject matter may be embodied in many different forms, reference will now be made in detail to specific embodiments of the disclosed subject matter. This description is an exemplification of the principles of the disclosed subject and is not intended to limit the invention to the particular embodiments illustrated.

The presently disclosed subject matter will be described in connection with a reformer unit in a refinery. The reformer unit is part of the refinery and one of the multiple units contained within the refinery that process hydrocarbons. The present invention is not intended to be so limited; rather, other processing units having a feed and a product output within the refinery are considered to be well within the scope of the present invention. Furthermore, it is intended that the disclosed subject matter may be utilized in non-refining environments where it is desirable to monitor either feedstock or product stream in order to monitor the operation of a processing unit.

The disclosed subject matter will be described utilizing a naphtha feedstock. The present invention is not intended to be so limited; rather other hydrocarbon feedstocks are considered to be well within the scope of the present invention and the correlation matrices disclosed herein are capable of being used in substantially the same manner as described herein. Feedstocks shall also contain in-process streams produced with the refinery and various combination of in-process streams and naphtha streams.

The disclosed subject matter will further be described in connection with the analysis of the feedstock fed into the reformer unit. While the analysis of the feedstock is most preferred, it is contemplated that the feedstock and/or the product output (e.g. reformate) may be analyzed.

The development of correlation matrices ($M_{CM}$) will now be described in greater detail. A feed sample for a given feedstock is analyzed. The same feed sample is analyzed using both detailed hydrocarbon analysis (DHA) and multi-dimensional gas chromatographic analysis (PIONA). Detailed hydrocarbon analysis is preferably performed using a single column gas chromatograph analyzer and utilizing one of the following ASTM methodologies: D6729, D6730, D6733 and D5134. When the refinery unit is a reformer, ASTM D5134 is the preferred methodology; however, other non-published methodologies that may use still higher resolution gas chromatographic separation columns with lengths up to 150 meters may also be used. The multi-dimensional gas chromatographic analysis (PIONA) is preferably performed using a complex multi-dimensional gas chromatograph analyzer and utilizing one of the following ASTM methodologies: D6839 and D5443. When the refinery unit is a reformer, ASTM D5443 is the preferred methodology. The present invention, however, is not intended to be limited to the use of any of the above mentioned ASTM methodologies; rather, other methodologies capable of identifying the composition of feedstock are well within the scope of the present invention.

Both the DHA analysis and the PIONA analysis identify individual compounds within the feedstock. The compounds can be classified by both carbon numbers and type (e.g., paraffins (P), olefins (O), naphthenes (N) and aromatics (A)). PIONA identifies all components by carbon number except for carbon numbers for which there is only one species present (e.g., benzene (C7 aromatic), toluene (C7 aromatic), cyclopentane (C5 naphthene), etc.). The conversion matrix can be developed by comparing the output from the DHA analysis for a given carbon number and type for the corresponding output from the PIONA analysis for the same sample.

The determination of the conversion matrices will now be described in connection with several examples. A naphtha feedstock for a given reformer unit was analyzed by both DHA analysis and PIONA analysis. Table 1 represents the output of the DHA analysis for a sample feedstock A run in a reformer unit 1. Each of the outputs listed in the below table represents a concentration vector $C_{DHA}$ for the components in the feedstock. For example, the $C_{DHA}$ for paraffins in the C-3 region is 0.57. The $C_{DHA}$ for aromatics in the C-7 region is 4.25.

TABLE 1

DHA Analysis of Naphtha Feedstock A in Reformer Unit 1

| | P | O | N | A | Normalized Vol % Total |
|---|---|---|---|---|---|
| C-3 | 0.57 | 0.00 | 0.00 | 0.00 | 0.57 |
| C-4 | 0.84 | 0.00 | 0.00 | 0.00 | 0.84 |
| C-5 | 1.92 | 0.01 | 0.15 | 0.00 | 2.07 |
| C-6 | 8.87 | 0.00 | 3.95 | 1.02 | 13.84 |
| C-7 | 15.16 | 0.00 | 8.50 | 4.25 | 27.91 |
| C-8 | 16.36 | 0.09 | 5.75 | 6.71 | 28.91 |
| C-9 | 13.35 | 0.04 | 5.30 | 3.41 | 22.10 |
| C-10 | 3.03 | 0.00 | 0.48 | 0.06 | 3.56 |
| C-11+ | 0.20 | 0.00 | 0.00 | 0.00 | 0.20 |
| Total | 60.30 | 0.13 | 24.13 | 15.45 | 100.00 |

Table 2 represents the output of the PIONA analysis for a sample feedstock A run in a reformer unit 1. Each of the outputs listed in the below table represents a concentration vector $C_{PIONA}$ for the components in the feedstock. For example, the $C_{PIONA}$ for paraffins in the C-3 region is 0.00. The $C_{PIONA}$ for aromatics in the C-7 region is 4.21.

TABLE 2

PIONA Analysis of Naphtha Feedstock A in Reformer Unit 1

| | P | O | N | A | Normalized Vol % Total |
|---|---|---|---|---|---|
| C-3 | 0.00 | 0.00 | 0.00 | 0.00 | 0.00 |
| C-4 | 0.93 | 0.00 | 0.00 | 0.00 | 0.93 |
| C-5 | 1.84 | 0.00 | 0.14 | 0.00 | 1.98 |
| C-6 | 8.68 | 0.06 | 3.97 | 1.00 | 13.71 |
| C-7 | 15.06 | 0.00 | 8.49 | 4.21 | 27.76 |
| C-8 | 15.79 | 0.00 | 7.66 | 5.81 | 29.26 |
| C-9 | 12.48 | 0.04 | 5.89 | 2.84 | 21.25 |
| C-10 | 3.71 | 0.00 | 1.31 | 0.00 | 5.02 |
| C-11+ | 0.09 | 0.00 | 0.00 | 0.00 | 0.09 |
| Total | 58.58 | 0.10 | 27.46 | 13.86 | 100.00 |

Table 1 and Table 2 illustrate that a variance exists between the output produced by the less costly and less accurate DHA analysis and the corresponding output produced by the more costly, but more accurate PIONA analysis. A comparison of the output reveals that there may be up to approximately 5% difference in naphthene content, 3% difference in paraffin content and 2% difference in aromatics content, between the PIONA and DHA analyses. These differences are not insignificant because they translate into multi-million dollars of margin improvement, per year, per reformer. The correlation matrices developed in accordance with the present invention for routinely used feedstocks will allow refinery operators to utilize less costly DHA analysis with more accurate results in order to capture some of the margin gains associated with the PIONA analysis.

It should be noted that the variance produced when DHA analysis and PIONA analysis are performed on the product output (e.g., thereformate) is not as significant. As such, the adjustments made by the $M_{CM}$ factors in the correlation will also not be as significant.

The $M_{CM}$ factor for each concentration vector is obtained using the following relationship with the concentration vectors obtained from the DHA analysis and the PIONA-RZA analysis.

$$M_{CM} = C_{PIONA} \div C_{DHA}$$

With reference to the output from Tables 1 and 2, the $M_{CM}$ factor for C-8 paraffins would be calculated as follows:

$$M_{CM} = 15.79 \div 16.36 = 0.96$$

With reference to the output from Tables 1 and 2, the $M_{CM}$ factor for C-9 aromatics would be calculated as follows:

$$M_{CM} = 2.84 \div 3.41 = 0.83$$

Table 3 illustrates the correlation matrix of $M_{CM}$ factors associated with the sample feedstock A run in the reformer unit 1.

TABLE 3

$M_{CM}$ Correlation For Naphtha Feedstock A in Reformer Unit 1

|      | P    | O    | N    | A    |
|------|------|------|------|------|
| C-3  | 0.00 | 0.00 | 0.00 | 0.00 |
| C-4  | 1.11 | 0.00 | 0.00 | 0.00 |
| C-5  | 0.96 | 0.00 | 0.97 | 0.00 |
| C-6  | 0.98 | 0.06 | 1.00 | 0.98 |
| C-7  | 0.99 | 0.00 | 1.00 | 0.99 |
| C-8  | 0.96 | 0.00 | 1.33 | 0.87 |
| C-9  | 0.93 | 1.00 | 1.11 | 0.83 |
| C-10 | 1.23 | 0.00 | 2.75 | 0.00 |
| C-11+| 0.45 | 0.00 | 0.00 | 0.00 |

Table 4 represents the output of the DHA analysis for the sample feedstock A run in another reformer unit, reformer unit 2, which run parallel to reformer unit 1. Each of the outputs listed in the below table represents a concentration vector $C_{DHA}$ for the components in the feedstock for reformer unit 2.

TABLE 4

DHA Analysis of Naphtha Feedstock A in Reformer Unit 2

|       | P      | O      | N      | A      | Normalized Vol % Total |
|-------|--------|--------|--------|--------|--------|
| C-3   | 0.000  | 0.000  | 0.000  | 0.000  | 0.000  |
| C-4   | 0.251  | 0.000  | 0.000  | 0.000  | 0.251  |
| C-5   | 3.417  | 0.006  | 0.262  | 0.000  | 3.685  |
| C-6   | 11.905 | 0.000  | 3.904  | 0.955  | 16.764 |
| C-7   | 16.497 | 0.000  | 8.034  | 3.412  | 27.943 |
| C-8   | 15.833 | 0.000  | 5.821  | 5.601  | 27.255 |
| C-9   | 11.127 | 0.035  | 3.649  | 3.273  | 18.084 |
| C-10  | 3.994  | 0.045  | 1.029  | 0.414  | 5.482  |
| C-11+ | 0.486  | 0.034  | 0.000  | 0.014  | 0.534  |
| Total | 63.510 | 0.120  | 22.699 | 13.669 | 99.998 |

Table 5 represents the output of the PIONA analysis for the sample feedstock A run in the reformer unit 2. Each of the outputs listed in the below table represents a concentration vector $C_{PIONA}$ for the components in the feedstock.

TABLE 5

PIONA Analysis of Naphtha Feedstock A in Reformer Unit 2

|       | P     | O    | N     | A     | Normalized Vol % Total |
|-------|-------|------|-------|-------|--------|
| C-3   | 0.00  | 0.00 | 0.00  | 0.00  | 0.00   |
| C-4   | 0.24  | 0.00 | 0.00  | 0.00  | 0.24   |
| C-5   | 3.33  | 0.00 | 0.25  | 0.00  | 3.58   |
| C-6   | 11.43 | 0.09 | 3.99  | 1.01  | 16.52  |
| C-7   | 16.20 | 0.00 | 8.23  | 3.52  | 27.95  |
| C-8   | 15.42 | 0.00 | 7.04  | 4.77  | 27.23  |
| C-9   | 10.75 | 0.06 | 4.80  | 2.62  | 18.23  |
| C-10  | 4.02  | 0.00 | 1.53  | 0.07  | 5.62   |
| C-11+ | 0.60  | 0.00 | 0.04  | 0.00  | 0.64   |
| Total | 61.99 | 0.15 | 25.88 | 11.99 | 100.01 |

A comparison of Tables 1 and 4 and Tables 2 and 5 reveals that the output of the DHA and PIONA analysis is refinery unit specific. The output of the analysis for reformer unit 1 differs from the output of the analysis of the same feedstock for reformer unit 2. As result, a separate correlation matrix is needed for the feedstock when it is fed into a separate reformer unit. The provision of a second correlation matrix for the second reformer unit will permit the monitoring of both units using the less costly DHA analysis methodology.

Table 6 illustrates the correlation matrix of $M_{CM}$ factors associated with the sample feedstock A run in the reformer unit 2.

TABLE 6

$M_{CM}$ Correlation For Naphtha Feedstock A in Reformer Unit 2

|       | P    | O    | N    | A    |
|-------|------|------|------|------|
| C-3   | 0.00 | 0.00 | 0.00 | 0.00 |
| C-4   | 0.96 | 0.00 | 0.00 | 0.00 |
| C-5   | 0.97 | 0.00 | 0.95 | 0.00 |
| C-6   | 0.96 | 0.09 | 1.02 | 1.06 |
| C-7   | 0.98 | 0.00 | 1.02 | 1.03 |
| C-8   | 0.97 | 0.00 | 1.21 | 0.85 |
| C-9   | 0.97 | 0.06 | 1.32 | 0.80 |
| C-10  | 1.01 | 0.00 | 1.49 | 0.17 |
| C-11+ | 1.23 | 0.00 | 0.04 | 0.00 |

Table 7 represents the output of the DHA analysis for a sample feedstock B (that is different from feedstock A) run in reformer unit 1. Each of the outputs listed in the below table represents a concentration vector $C_{DHA}$ for the components of feedstock B for reformer unit 1.

TABLE 7

DHA Analysis of Naphtha Feedstock B in Reformer Unit 1

|       | P      | O     | N      | A      | Normalized Vol % Total |
|-------|--------|-------|--------|--------|--------|
| C-3   | 0.000  | 0.000 | 0.000  | 0.000  | 0.000  |
| C-4   | 0.199  | 0.000 | 0.000  | 0.000  | 0.199  |
| C-5   | 2.255  | 0.000 | 0.181  | 0.000  | 2.436  |
| C-6   | 10.389 | 0.000 | 2.771  | 0.649  | 13.809 |
| C-7   | 14.658 | 0.000 | 5.267  | 2.762  | 22.687 |
| C-8   | 16.257 | 0.000 | 4.066  | 5.995  | 26.318 |
| C-9   | 13.922 | 0.051 | 3.959  | 5.397  | 23.329 |
| C-10  | 7.794  | 0.110 | 1.592  | 0.915  | 10.411 |
| C-11+ | 0.805  | 0.005 | 0.000  | 0.000  | 0.810  |
| Total | 66.279 | 0.166 | 17.836 | 15.718 | 99.999 |

Table 8 represents the output of the PIONA analysis for the sample feedstock A run in the reformer unit 2. Each of the outputs listed in the below table represents a concentration vector $C_{PIONA}$ for the components in the feedstock.

TABLE 8

PIONA Analysis of Naphtha Feedstock B in Reformer Unit 1

|  | P | O | N | A | Normalized Vol % Total |
|---|---|---|---|---|---|
| C-3 | 0.00 | 0.00 | 0.00 | 0.00 | 0.00 |
| C-4 | 0.19 | 0.00 | 0.00 | 0.00 | 0.19 |
| C-5 | 2.25 | 0.00 | 0.18 | 0.00 | 2.43 |
| C-6 | 10.20 | 0.09 | 2.79 | 0.65 | 13.73 |
| C-7 | 14.45 | 0.00 | 5.24 | 2.82 | 22.51 |
| C-8 | 15.47 | 0.04 | 5.15 | 5.04 | 25.70 |
| C-9 | 13.34 | 0.07 | 4.50 | 4.87 | 22.78 |
| C-10 | 8.84 | 0.00 | 2.28 | 0.18 | 11.30 |
| C-11+ | 1.37 | 0.00 | 0.00 | 0.00 | 1.37 |
| Total | 66.11 | 0.20 | 20.14 | 13.56 | 100.01 |

A comparison of Tables 1 and 7 and Tables 2 and 8 reveals that the output of the DHA and PIONA analysis is feedstock specific. The output of the analysis for feedstock A differs from the output of the analysis of feedstock B for the same reformer unit. As result, a separate correlation matrix is needed for each type of feedstock(s). The provision of a second correlation matrix for the second feedstock will permit the monitoring of the unit when different types of feedstocks are used using the less costly DHA analysis methodology.

Table 9 illustrates the correlation matrix of $M_{CM}$ factors associated with the sample feedstock B run in the reformer unit 1.

TABLE 9

$M_{CM}$ Correlation For Naphtha Feedstock B in Reformer Unit 1

|  | P | O | N | A |
|---|---|---|---|---|
| C-3 | 0.00 | 0.00 | 0.00 | 0.00 |
| C-4 | 0.95 | 0.00 | 0.00 | 0.00 |
| C-5 | 1.00 | 0.00 | 0.99 | 0.00 |
| C-6 | 0.98 | 0.09 | 1.01 | 1.00 |
| C-7 | 0.99 | 0.00 | 0.99 | 1.02 |
| C-8 | 0.95 | 0.04 | 1.27 | 0.84 |
| C-9 | 0.96 | 1.37 | 1.14 | 0.90 |
| C-10 | 1.13 | 0.00 | 1.43 | 0.20 |
| C-11+ | 1.70 | 0.00 | 0.00 | 0.00 |

As discussed above, the correlation matrices produced in accordance with aspects of the present invention are refinery, feedstock and reformer unit specific. The specifics of the refinery include the piping details leading to reforming unit impact the operation of the reformer unit and may impact the selection of the appropriate correlation matrices. It is contemplated that each reformer unit will have multiple correlation matrices corresponding to the type of feedstocks run through the reformer unit. Furthermore, it is contemplated that each feedstock will have multiple correlation matrices corresponding to the different reformer units through which the feedstock is fed. It is contemplated that each refinery will have a database containing the multiple correlation matrices for use in connection with the monitoring and optimizing the operation of the reformer units. Refinery operation experiences indicates that for a given refinery there will be only finite types of feedstocks and finite types of reforming outputs feasible. This renders the correlation matrices approach mathematically/computationally manageable.

The selection of the proper correlation matrix $M_{CM}$ will serve the function of converting less precise $C_{DHA}$ analysis to more precise $C_{PIONA}$ analysis. The proper correlation matrix is selected based upon the known analytical hydrocarbon composition data of identical or similar feedstocks; factoring compositional differences amongst different naphtha feeds and the constraints of the reforming facilities including the piping, etc leading to the reforming unit. As such, less costly DHA analysis can be used on a regular basis (e.g., daily, weekly, monthly) to predict the output of more costly PIONA analysis. The day-to-day DHA test data analysis of changing feed and reforming products will then allow the less accurate DHA testing results, widely available in most refineries, to be re-expressed in the form of more accurate PIONA counterparts. The correlation matrices function as multi-dimensional correction factors, to convert the single dimensional DHA data to the multi-dimensional PIONA data.

The correlation matrices in accordance with the presently disclosed subject matter are intended to be used in refineries that are not equipped with PIONA multi-dimensional gas chromatographic analysis equipment or as a less costly alternative to PIONA analysis. The advantage of deploying such correlation matrices is to allow the refineries to convert DHA output into equivalent PIONA output. Thus providing the refinery with the ability to attain margin improvement normally associated with PIONA analysis.

The use of the correlation matrices will now be described in great detail. A sample of feedstock will be analyzed using the same DHA analysis methodology used to produce the matrices. The individual compounds of the feedstock will be grouped by carbon number and type in a similar format to that described in Tables 1, 2, 4, 5, 7 and 8. Table 10 is a generic representation of the DHA analysis output for the feedstock.

TABLE 10

Generic Representation of DHA Analysis of Naphtha Feedstock in Reformer Unit

|  | P | O | N | A | Normalized Vol % Total |
|---|---|---|---|---|---|
| C-3 | P3 | O3 | N3 | A3 | —.— |
| C-4 | P4 | O4 | N4 | A4 | —.— |
| C-5 | P5 | O5 | N5 | A5 | —.— |
| C-6 | P6 | O6 | N6 | A6 | —.— |
| C-7 | P7 | O7 | N7 | A7 | —.— |
| C-8 | P8 | O8 | N8 | A8 | —.— |
| C-9 | P9 | O9 | N9 | A9 | —.— |
| C-10 | P10 | O10 | N10 | A10 | —.— |
| C-11+ | P10 | O11 | N11 | A11 | —.— |
| Total | —.— | —.— | —.— | —.— | 100.00 |

A suitable correlation matrix will be selected based upon the feedstock characteristics and the particular reforming unit. Table 11 is a representative sample of the correlation matrix associated with the particular type of feedstock and reformer unit.

TABLE 11

Generic Representation $M_{CM}$ Correlation For Naphtha Feedstock in Reformer Unit

|  | P | O | N | A |
|---|---|---|---|---|
| C-3 | B3 | C3 | D3 | E3 |
| C-4 | B4 | C4 | D4 | E4 |
| C-5 | B5 | C5 | D5 | E5 |
| C-6 | B6 | C6 | D6 | E6 |
| C-7 | B7 | C7 | D7 | E7 |
| C-8 | B8 | C8 | D8 | E8 |
| C-9 | B9 | C9 | D9 | E9 |
| C-10 | B10 | C10 | D10 | E10 |
| C-11+ | B11 | C11 | D11 | E11 |

The appropriate $M_{CM}$ factor for each carbon number and type pairing will then be applied in the following relationship:

$$C_{DHA} \times M_{CM} = C_{PIONA\text{-}EQUIVALENT}$$

The use of the correlation matrices will produce a PIONA equivalent output. A sample of the equivalent output using the above relationship is set forth in Table 12.

TABLE 12

Generic Representation of PIONA Equivalent Analysis of Naphtha Feedstock in Reformer Unit

| | P | O | N | A | Normalized Vol % Total |
|---|---|---|---|---|---|
| C-3 | P3xB3 | O3xC3 | N3xD3 | A3xE3 | —.— |
| C-4 | P4xB4 | O4xC4 | N4xD4 | A4xE4 | —.— |
| C-5 | P5xB5 | O5xC5 | N5xD5 | A5xE5 | —.— |
| C-6 | P6xB6 | O6xC6 | N6xD6 | A6xE6 | —.— |
| C-7 | P7xB7 | O7xC7 | N7xD7 | A7xE7 | —.— |
| C-8 | P8xB8 | O8xC8 | N8xD8 | A8xE8 | —.— |
| C-9 | P9xB9 | O9xC9 | N9xD9 | A9xE9 | —.— |
| C-10 | P10xB10 | O10xC10 | N10xD10 | A11xE10 | —.— |
| C-11+ | P11xB11 | O11xC11 | N11xD11 | A11xE11 | —.— |
| Total | —.— | —.— | —.— | —.— | 100.00 |

The PIONA equivalent output may then be input into an appropriate reforming model that is used to predict product yields, hydrogen production, etc. The model is then run to determine what modifications if any are needed to (i) modify or re-optimize reforming unit operation, or (ii) modify reforming unit operation to produce a desired product output based upon the given type of feedstock. As such, it would be possible to adjust in real time the operation of the reformer unit to modify or change the product output in response to market conditions for a given product (i.e., modify output to produce more or less of a given product based upon need). As discussed above, the PIONA analysis is considered more accurate than the less costly DHA analysis. The use of the PIONA analysis in the appropriate model results in greater optimization of the reformer unit with the desired product output. The correlation matrices of the presently disclosed subject matter through the use of PIONA equivalent analysis permit the use of less costly DHA analysis with the results of the more costly PIONA analysis. It is anticipated that the improvements in the operation of the reforming unit based upon the PIONA equivalent analysis may result in multi-million dollar savings to the refinery.

It is contemplated that the output of the DHA analysis for a feedstock sample may be fed into a control unit or computer system. The operator may then enter the appropriate information relating to the type of feedstock and the particular reforming unit such that the appropriate correlation matrix may then be selected. It is contemplated that this operation of selecting the appropriate matrix and the subsequent correlation conversion to PIONA equivalent output will be performed by the control unit. The information may then be automatically fed to the appropriate model to determine whether or not adjusts to the reformer unit are needed in order to re-optimize operation or modify the product output.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Although, the correlation factors $M_{CM}$ are expressed in simple ratios in present invention, it is possible to develop or extend the concept of correlation for DHA vs PIONA by using more sophisticated approaches, such as use of chemometrics etc. As such, a larger data base that uses in more detail the entire DHA (isomeric fingerprinting) and PIONA (carbon number distributions) for feedstocks at a given refinery for a given reactor can be generated. The data base can then be used to develop a more complex correlation model.

The invention claimed is:

1. A method of monitoring a refinery unit, wherein the refinery unit having a feedstock supplied thereto and at least one product stream withdrawn therefrom, the method comprising:
   analyzing at least one of the feedstock and the product stream, wherein the analyzing includes performing a detailed hydrocarbon analysis of at least one of the feedstock and the product stream; wherein performing the detailed hydrocarbon analysis includes utilizing a one-dimensional single column gas chromatograph;
   obtaining a one-dimensional output from the detailed hydrocarbon analysis; and
   adjusting the one-dimensional output to produce a multi-dimensional gas chromatographic equivalent output.

2. The method according to claim 1, wherein adjusting the one-dimensional output includes applying a correlation matrix to the one-dimensional output to produce the multi-dimensional gas chromatographic equivalent output; wherein the correlation matrix is based upon characteristics of the feedstock and the particular refinery unit; wherein the correlation matrix is further based upon both one dimensional single column gas chromatography and multi-dimensional gas chromatography on the feedstock of the particular refinery unit.

3. The method according to claim 1, further comprising: optimizing the operation of the refinery unit based upon the multi-dimensional gas chromatographic equivalent output.

4. The method according to claim 3, wherein the refinery unit is a reformer unit and the feedstock includes at least one of an in-process stream and a naphtha feedstock.

5. The method according to claim 3, wherein the multi-dimensional gas chromatographic equivalent output is input in a unit performance model to optimize the operation of the refinery unit.

6. The method according to claim 5, further comprising: obtaining an output from the unit performance model; and adjusting the operation of the refinery unit based upon the output from the unit performance model.

7. The method according to claim 6, wherein the refinery unit is a reformer unit and the feedstock includes at least one of an in-process stream and a naphtha feedstock.

8. The method according to claim 1, further comprising: adjusting the operation of the refinery unit based upon the multi-dimensional gas chromatographic equivalent output to adjust product output from the refinery unit.

9. The method according to claim 8, wherein the refinery unit is a reformer unit and the feedstock includes at least one of an in-process stream and a naphtha feedstock.

10. The method according to claim 8, wherein the multi-dimensional gas chromatographic equivalent output is input in a unit performance model to modify the operation of the refinery unit to modify the product stream from the refinery unit.

11. The method according to claim 10, further comprising: obtaining an output from the unit performance model; and adjusting the operation of the refinery unit based upon the output from the unit performance model.

12. The method according to claim 11, wherein the refinery unit is a reformer unit and the feedstock includes at least one of an in-process stream and a naphtha feedstock.

13. The method of claim 1, wherein analyzing at least one of the feedstock and the product stream includes analyzing the feedstock.

14. The method according to claim 13, wherein the refinery unit is a reformer unit and the feedstock includes at least one of an in-process stream and a naphtha feedstock.

15. A method of optimizing the operation of reformer unit, wherein the reformer unit having a naphtha feedstock supplied thereto and at least one product stream withdrawn therefrom, the method comprising:
    analyzing at least one of the feedstock and the product stream, wherein the analyzing includes performing a detailed hydrocarbon analysis of at least one of the feedstock and the product stream; wherein performing the detailed hydrocarbon analysis includes utilizing a one-dimensional single column gas chromatograph;
    obtaining a one-dimensional output from the detailed hydrocarbon analysis;
    adjusting the one-dimensional output to produce a multi-dimensional gas chromatographic equivalent output; and
    optimizing the operation of the reformer unit based upon the multi-dimensional gas chromatographic equivalent output.

16. The method according to claim 15, wherein adjusting the one-dimensional output includes applying a correlation matrix to the one-dimensional output to produce the multi-dimensional gas chromatographic equivalent output; wherein the correlation matrix is based upon characteristics of the naphtha feedstock and the particular reformer unit; wherein the correlation matrix is further based upon both one dimensional single column gas chromatography and multi-dimensional gas chromatography on the naphtha feedstock of the particular reformer unit.

17. The method according to claim 15, wherein optimizing the operation of the reformer unit includes inputting the multi-dimensional as chromatographic equivalent output to a unit performance model to optimize the operation of the reformer unit.

18. The method according to claim 17, further comprising: obtaining an output from the unit performance model; and adjusting the operation of the reformer unit based upon the output from the unit performance model.

19. The method of claim 15, wherein analyzing at least one of the feedstock and the product stream includes analyzing the feedstock.

20. A method of modifying the operation of reformer unit to adjust a product stream produced therefrom, wherein the reformer unit having a naphtha feedstock supplied thereto and at least one product stream withdrawn therefrom, the method comprising:
    analyzing at least one of the feedstock and the product stream, wherein the analyzing includes performing a detailed hydrocarbon analysis of at least one of the naphtha feedstock and the product stream; wherein performing the detailed hydrocarbon analysis includes utilizing a one-dimensional single column gas chromatograph;
    obtaining a one-dimensional output from the detailed hydrocarbon analysis;
    adjusting the one-dimensional output to produce a multi-dimensional gas chromatographic equivalent output; and
    modifying the operation of the reformer unit based upon the multi-dimensional gas chromatographic equivalent output to modify the product stream from the reformer unit.

21. The method according to claim 20, wherein modifying the operation includes inputting the multi-dimensional gas chromatographic equivalent output into a unit performance model to modify the operation of the reformer unit to modify the product stream from the reformer unit.

22. The method according to claim 21, further comprising: obtaining an output from the unit performance model; and adjusting the operation of the reformer unit based upon the output from the unit performance model.

23. The method of claim 20, wherein analyzing at least one of the feedstock and the product stream includes analyzing the feedstock.

* * * * *

UNITED STATES PATENT AND TRADEMARK OFFICE
CERTIFICATE OF CORRECTION

| | | Page 1 of 1 |
|---|---|---|
| PATENT NO. | : 9,063,115 B2 | |
| APPLICATION NO. | : 13/896485 | |
| DATED | : June 23, 2015 | |
| INVENTOR(S) | : Frank DiSanzo et al. | |

It is certified that error appears in the above-identified patent and that said Letters Patent is hereby corrected as shown below:

On the Title Page, Item (60), under "Related U.S. Application Data", replace "Provisional application No. 61/653,023, filed on May 30, 2013" with "Provisional application No. 61/653,023, filed on May 30, 2012."

Signed and Sealed this
Twelfth Day of January, 2016

Michelle K. Lee
*Director of the United States Patent and Trademark Office*